(12) United States Patent
Wallukat

(10) Patent No.: US 7,741,050 B2
(45) Date of Patent: Jun. 22, 2010

(54) IDENTIFICATION OF AGONISTIC AUTOANTIBODIES

(75) Inventor: Gerd Wallukat, Berlin (DE)

(73) Assignee: Max-Delbrueck-Centrum fuer Molkulare Medizin (DE)

(*) Notice: Subject to any disclaimer, the term of this patent is extended or adjusted under 35 U.S.C. 154(b) by 954 days.

(21) Appl. No.: 10/536,552

(22) PCT Filed: Nov. 28, 2003

(86) PCT No.: PCT/DE03/03988

§ 371 (c)(1),
(2), (4) Date: Jan. 26, 2006

(87) PCT Pub. No.: WO2004/051280

PCT Pub. Date: Jun. 17, 2004

(65) Prior Publication Data

US 2006/0263835 A1    Nov. 23, 2006

(30) Foreign Application Priority Data

Nov. 29, 2002 (DE) .............................. 102 56 897
Jan. 27, 2003 (DE) .............................. 103 03 120
Jun. 13, 2003 (DE) .............................. 103 27 066

(51) Int. Cl.
*G01N 33/537* (2006.01)
*G01N 33/538* (2006.01)
*G01N 33/564* (2006.01)

(52) U.S. Cl. ...................... 435/7.1; 435/7.92; 435/7.95; 435/971; 436/506; 436/538; 436/541

(58) Field of Classification Search ....................... None
See application file for complete search history.

(56) References Cited

U.S. PATENT DOCUMENTS

| | | | | |
|---|---|---|---|---|
| 4,468,470 | A | * | 8/1984 | Aalberse ...................... 436/539 |
| 6,994,970 | B1 | * | 2/2006 | Ronspeck et al. .............. 435/6 |
| 7,309,488 | B2 | * | 12/2007 | Ogino et al. ............. 424/140.1 |

FOREIGN PATENT DOCUMENTS

| | | |
|---|---|---|
| DE | 101 23 929 A1 | 11/2002 |
| WO | 00/39154 A2 | 7/2000 |
| WO | WO 01/21660 * | 3/2001 |
| WO | 02/16431 A2 | 2/2002 |
| WO | 2004/067549 A2 | 8/2004 |

OTHER PUBLICATIONS

Lederman et al, Molec. Immunol., 28, 1171-1181, 1991.*
Staudt Alexander et al: "Potential role of autoantibodies belonging to the immunoglobulin G-3 subclass in cardiac dysfunction among patients with dilated cardiomyopathy." Circulation, vol. 106, No. 19, 2002, pp. 2448-2453.*
Wallukat G et al: "Anti-Betai-Adrenoceptor Autoantibodies With Chronotropic Activity From the Serum of Patients With Dilated Cardiohyopathy: Mapping of Epitopes in the First and Second Extracellular Loops." Journal of Molecular and Cellular Cardiology, vol. 27, 1995, pp. 397-406.*
Harlow et al, Antibodies: A Laboratory Manual, Cold Spring Harbor Laboratory, 1988, pp. 298-299.*
* Wallukat Gerd et al: "Spontaneously beating neonatal rat heart myocyte culture: A model to characterize angiotensin II AT1 receptor autoantibodies in patients with preeclampsia." in: In Vitro Cellular and Developmental Biology Animal, vol. 38, No. 7, 2002, pp. 376-377.
* Wallukat Gerd et al: "Specific removal of beta1-adrenergic autoantibodies from patients with idiopathic dilated cardiomyopathy." in: New England Journal of Medicine, vol. 347, No. 22, Nov. 28, 2002, p. 1806.
* Wallukat Gerd et al: "Autoantibodies against the beta- and muscarinic receptors in cardiomyopathy"in: HERZ, vol. 25, No. 3, 2000, pp. 261-266.
* Fu Michael L X et al: "A synthetic Peptide corresponding to the second extracellular loop of the human M2 acetylcholine receptor induces pharmacological and morphological changes in cardiomyocytes by active immunization after 6 months in rabbits" Clinical Immunology and Immunopathology, vol. 78, No. 2, 1996, pp. 203-207.
* Marino Maria et al: "Prevention of systemic lupus erythematosus in MRL/Ipr mice by administration of an immunoglobulin-binding peptide" . Nature Biotechnology, vol. 18, No. 7, Jul. 2000, pp. 735-739.
* Boros Peter et al: "Specificity and class distribution of Fc-gamma-R-specific autoantibodies in patients with autoimmune disease" in: Journal of Immunology, The Williams and Wilkins Co. Baltimore, US, vol. 152, 1994, pp. 302-306.
* MacFarlane S R et al: "Proteinase-activated receptors" in: Pharmacological Reviews, Williams and Wilkins Inc., Baltimore, MD,, US, vol. 53, No. 2, Jun. 2001, pp. 245-282.
* Belch J J F: "Raynaud's phenomenon" in: Current Opinion in Rheumatology, vol. 3, No. 6, 1991, pp. 960-966.
Dragun D et al: "Patients With Steroid Refractory Acute Vascular Rejection Develop Agonistic Antibodies Targeting Angiotensin II Type 1 Receptor" in: Transplantation Proceedings, vol. 35, No. 6, Sep. 6, 2003, pp. 2104-2105.
Dragun D et al: "Steroid-Resistant Vascular Rejection Due to Agonistic ATI-Receptor Antibodies Causing Expression of TF, MCP-1, and RANTES" in: Journal of the American Society of Nephrology, vol. 12, Sep. 2001, p. 930A.
Luther et al: "Alpha1-adrenergic receptor antibodies in patients with primary hypertension" in: Hypertension, vol. 29, No. 2, 1997, pp. 678-682.
Liao et al: "Autoantibodies against AT1-receptor and alpha1-adrenergic receptor in patients with hypertension" in: Official Journal of the Japanese Society of Hypertension, vol. 25, No. 4, Jul. 2002, pp. 641-646.
Fu et al: "Functional autoimmune epitope on alpha 1-adrenergic receptors in patients with malignant hypertension" in: Lancet, vol. 344, No. 8938, 1994, p. 1660.

* cited by examiner

*Primary Examiner*—David A Saunders
(74) *Attorney, Agent, or Firm*—Joyce v. Natzmer; Pequignot + Myers

(57) ABSTRACT

The invention relates to a method for detecting disease-associated autoantibodies, which recognize extracellular structures of G protein-coupled receptors, and to the use of peptides, which comprise these loops or fragments thereof, for treating autoimmune diseases.

13 Claims, 1 Drawing Sheet

SEQUENCE LISTING

```
<160> NUMBER OF SEQ ID NOS: 16

<210> SEQ ID NO 1
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 1

Glu Tyr Gly Ser Phe Phe
1               5

<210> SEQ ID NO 2
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 2

Ser Phe Phe Cys Glu Leu
1               5

<210> SEQ ID NO 3
<211> LENGTH: 7
<212> TYPE: PRT
<213> ORGANISM: Artificial
<220> FEATURE:
<223> OTHER INFORMATION: Description of the artificial sequence: peptide

<400> SEQUENCE: 3

Ala Arg Arg Cys Tyr Asn Asp
1               5

<210> SEQ ID NO 4
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 4
```

```
Pro Lys Cys Cys Asp Phe
1               5
```

<210> SEQ ID NO 5
<211> LENGTH: 5
<212> TYPE: PRT
<213> ORGANISM: Artificial
<220> FEATURE:
<223> OTHER INFORMATION: Description of the artificial sequence: peptide

<400> SEQUENCE: 5

```
Ala Glu Ser Asp Glu
1               5
```

<210> SEQ ID NO 6
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 6

```
Cys Tyr Ile Gln Phe Phe
1               5
```

<210> SEQ ID NO 7
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 7

```
Glu Asp Gly Glu Cys Tyr
1               5
```

<210> SEQ ID NO 8
<211> LENGTH: 25
<212> TYPE: PRT
<213> ORGANISM: Artificial
<220> FEATURE:
<223> OTHER INFORMATION: Description of the artificial sequence: peptide

<400> SEQUENCE: 8

```
Val Arg Thr Val Glu Asp Gly Glu Cys Tyr Ile Gln Phe Phe Ser Asn
1               5                   10                  15

Ala Ala Val Thr Phe Gly Thr Ala Ile
            20                  25
```

<210> SEQ ID NO 9
<211> LENGTH: 7
<212> TYPE: PRT
<213> ORGANISM: Artificial
<220> FEATURE:
<223> OTHER INFORMATION: Description of the artificial sequence: peptide

<400> SEQUENCE: 9

```
Ala Phe His Tyr Glu Ser Gln
1               5
```

<210> SEQ ID NO 10
<211> LENGTH: 6
<212> TYPE: PRT
<213> ORGANISM: Artificial
<220> FEATURE:
<223> OTHER INFORMATION: Description of the artificial sequence: peptide

```
<400> SEQUENCE: 10

Glu Asn Thr Asn Ile Thr
1               5

<210> SEQ ID NO 11
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 11

Phe Trp Ala Phe Gly Arg
1               5

<210> SEQ ID NO 12
<211> LENGTH: 7
<212> TYPE: PRT
<213> ORGANISM: Artificial
<220> FEATURE:
<223> OTHER INFORMATION: Description of the artificial sequence: peptide

<400> SEQUENCE: 12

Gly Arg Ala Phe Cys Asp Val
1               5

<210> SEQ ID NO 13
<211> LENGTH: 7
<212> TYPE: PRT
<213> ORGANISM: Artificial
<220> FEATURE:
<223> OTHER INFORMATION: Description of the artificial sequence: peptide

<400> SEQUENCE: 13

Ile Thr Glu Glu Ala Gly Tyr
1               5

<210> SEQ ID NO 14
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 14

Glu Arg Phe Cys Gly Ile
1               5

<210> SEQ ID NO 15
<211> LENGTH: 6
<212> TYPE: PRT
<213> ORGANISM: Artificial
<220> FEATURE:
<223> OTHER INFORMATION: Description of the artificial sequence: peptide

<400> SEQUENCE: 15

Gly Arg Ile Phe Cys Asp
1               5

<210> SEQ ID NO 16
<211> LENGTH: 8
<212> TYPE: PRT
<213> ORGANISM: Artificial
<220> FEATURE:
<223> OTHER INFORMATION: Description of the artificial sequence: peptide

<400> SEQUENCE: 16
```

```
Ile Thr Thr Cys His Asp Val Leu
1               5
```

IDENTIFICATION OF AGONISTIC AUTOANTIBODIES

Figure 1:

The invention relates to a method for detecting disease-associated autoantibodies, which bind loops of G protein-coupled receptors, and to the use of peptides, which comprise these loops or fragments thereof, for treating autoimmune diseases.

The immune system of multicellular organisms is based on the differentiation between "self" and "not self". Because of its great diversity, the immune system that differentiates between "self" and "not self" has at its disposal a large repertoire of specificities, which are expressed particularly by T cells and B cells. By means of complicated mechanisms, the immune system is enabled to differentiate between "self" and "not self," with which mechanisms the body can protect itself, in particular, against the consequences of so-called autoimmunity. This means that the humoral and cellular components of the immune system of an organ are marked in such a manner that they do not direct themselves against the organism itself. However, many different types of disturbances can occur within the immune system; in particular, the mechanisms of self-recognition can be restricted or completely eliminated. Therefore there are a number of diseases that can be triggered by autoantibodies or autoreactive T cells. One of the first diseases in which autoantibodies against a specific organ were found, is Hashimoto thyroiditis. This is a disease of the thyroid that occurs mainly in middle-aged women and leads to the formation of a goiter and hypofunction of the thyroid. If the disease is not treated, complete destruction and shrinkage of the organ occur. Aside from autoantibodies that are directed exclusively against an organ, there are numerous autoantibodies that can be directed against several organs or tissue types.

In accordance with the orientation of the autoantibody, a differentiation can be made between organ-specific and non-organ-specific autoimmune diseases. Typical organ-specific autoimmune diseases are, for example, premature menopause, juvenile diabetes, male infertility, pernicious anemia or Addison's disease. The non-organic specific autoimmune diseases include, for example, rheumatoid arthritis, dermatomyositis, scleroderma, or mixed connective tissue diseases and others. Frequently, target organs affected by organ-specific disease are the thyroid, the adrenal gland, the stomach, and the pancreas, while the non-organ-specific diseases are summarized by the term of the so-called rheumatic form group, and relate to the skin, the kidneys, the joints and the muscles. Up to the present, only a few, inadequate methods have become known for the diagnosis and treatment of autoimmune diseases. Using the known laboratory routines, such as ELISA, or other diagnostic methods that have become established, which have proven themselves in mass screening under the laboratory conditions of a clinic, for example, it is not possible to detect the autoantibodies in the serum of a patient, which are often present only in small concentrations. Treatment in the case of organ-specific diseases takes place, in most cases, by restoring the metabolic equilibrium; for example, in the case of thyroid hypofunction, the missing thyroid hormone is substituted with thyroxin, and in the case of thyrotoxicosis, antimetabolites of the hormone can be administered. In pernicious anemia, a depot of vitamin $B_{12}$ can be administered parenterally, and in myasthenia gravis, cholinesterase inhibitors can be administered. If a complete loss of function of an organ has occurred, an organ transplant or implantation of a prosthesis, for example, are possible. Such therapeutic methods are not suitable in the case of non-organ-specific autoimmune diseases, since here, for example, an entire group of organs, such as the skin, the kidneys, the joints, and the muscles, would have to be substituted in a patient, whereby substitution of the joints, the muscles and/or the skin, alone, is almost impossible. Another possibility for treating autoimmune diseases is to bind the autoantibody that induces the disease, to complex it, and consequently to eliminate it from the serum. Such methods can, however, only be successfully used in diagnosis or therapy if a target, an agent, or a structure are known, with which the autoantibodies interact in such a manner, that they can be detected or eliminated using the agent or the target. For numerous autoimmune diseases, for example autoantibody-associated hypertension, preeclampsia, and Chagas' cardiomyopathy, such agents are not known. Previous diagnosis methods, such as bioassays, are difficult to handle and are therefore not suited for laboratory routine. Known bioassays are, for example, cardiomyocyte cultures for detecting angiotensin II AT1 receptor autoantibodies.

It was therefore an object of the invention to make available means, devices, and methods for the diagnosis of autoantibodies and the treatment of autoimmune diseases, which allow simple, efficient, and reliable detection or treatment, and which do not demonstrate the disadvantages stated.

The invention solves this technical problem by means of making available a method for the detection of disease-associated autoantibodies, which are directed against G protein-coupled receptors, whereby the method comprises the following steps:
 a) Bringing bodily fluid into contact with a denaturing agent,
 b) Bringing the precipitated fraction into contact with a peptide, particularly one comprising biotin, which comprises a partial sequence of the first and/or second loop of the receptor, whereby a mixture is formed,
 c) Incubating the mixture with a carrier, particularly one coated with avidin or streptavidin,
 d) Washing the materials of the carrier,
 e) Incubating the carrier with anti-IgG subclasses, whereby the anti-IgG antibody is marked, and
 f) Carrying out a detection reaction, particularly an enzyme reaction or color reaction.

In other words, the invention relates to the surprising teaching that it is possible to detect disease-associated autoantibodies, which are particularly directed against G protein-coupled receptors, using an enzyme reaction or color reaction, for example in an ELISA, a customary laboratory routines. This particularly relates to autoantibodies, which are connected with the diseases of dilatative cardiomyopathy, Chargas' cardiomyopathy, myocarditis, preeclampsia, malignant hypertension, essential hypertension, refractory hypertension, pulmonary hypertension, psoriasis and/or Raynaud's syndrome; preferably. Preferably, the antibodies are agonistic autoantibodies. Preferably, these diseases can be detected simply, more reliably and effectively using an inventive enzyme-coupled immune test. Such diseases, particularly the antibodies associated with them, could only be detected, until now, using complicated indirect tests, such as bioassays. Thus, angiotensin II-AT1 receptor autoantibodies, which are associated with preeclampsia, for example, were detected reliably until now only by bringing the sera, in each instance, into contact with cultivated cardiomyocytes, particularly those of newborn rats, by way of a modification in the heart rate. For this purpose, it was necessary to culture the cardiomyocytes of newborn rats and to bring them into contact with the serum of the patients, whereby antibodies against the AT1 receptor could be detected in patients having preeclampsia, by means of the detection of the increase in the beats per minute. Using the inventive method, an immune test is made available with which numerous autoantibodies that are directed against G protein-coupled receptors can be detected. These autoantibodies are preferably an autoantibody directed against a beta1-adrenergen receptor, an autoantibody directed against a muscarinergen M2 receptor, an angiotensin II AT1 receptor autoantibody, an alpha1-adrenergen receptor autoantibody, and autoantibodies that are directed against endothelin IA, PAR-1, PAR-2, and/or PAR-3. The autoantibodies can, in particular, be autoantibodies having an agonistic effect. Of course the antibodies can also be inhibitive antibodies, e.g. in allergic asthma (interaction with the $3^{rd}$ loop). Such a streptavidin-coated carrier is a carrier, which is coated preferably with streptavidin or avidin. Particularly preferred are proteins consisting of 6 to 2, particularly 4 subunits, $M_R$ approximately 40,000 to 80,000, particularly 60,000 or 66,000, isoelectric point close to the neutral point, such as streptavidin or avidin, for example, which demonstrate a high affinity (e.g. $K_D = 10^{-15}$ $M^{-1}$) to other compounds, particularly those inactivating by means of choline, preferably biotin. It is known to a person skilled in the art that a carrier, particularly one coated with streptavidin, is advantageous, if a structure that can be connected in effect with the latter is associated with biotin or an equivalent. If it is determined experimentally that the bond is sufficient for detection even without a biotin/streptavidin/avidin association or bond, the peptide or the carrier does not have to be bound to these ancillary substances (biotin and streptavidin/avidin).

In the sense of the invention, the peptide is a molecule, which consists essentially of amino acids. Peptides in the sense of the invention are also structures, which comprise more than 50 or 100 amino acids, respectively, and therefore can also be referred to as proteins. Peptides and proteins are therefore used synonymously in connection with the invention. Of course, the peptides may comprise other structures such as lipids or carbohydrates, but also artificial or natural amino acid modules or non-amino acid modules.

The peptide or protein comprising biotin can also be combined with a tag other than biotin. In the sense of the invention, a tag is a protein tag or a peptide or another structure, which is combined with, for example, fused to the peptide or protein. The peptide may, as already explained, be present in biotinylated form, and therefore have biotin as the tag. A person skilled in the art is familiar with other tag structures or tags, from catalogs and standard works in biochemistry. Preferred tags are His tag, Flag tag, Strep tag, T7 tag (1 N-terminal amino acids of the T7Gen10 protein), S tag, CBP (calmodulin binding peptide), MBP (maltose binding peptide), Neb, Protein A, GST tag, PinPoint tag, thioredoxin, PET (cellulose binding domain), Pmal (maltose binding domain), and/or biotin tag. This tag possesses a high affinity for an anti-tag substance or an anti-tag on the carrier. Preferred anti-tags are streptavidin, glutathione, biotin, nickel-NTA, cellulose, amylose, thiobond, avidin, and/or immunoglobulin. A person skilled in the art is familiar with tag/anti-tag pairs, i.e. the selection of the tag determines the structure of the anti-tag, without an inventive selection by the person skilled in the art being required, or such person first having to solve a technical task in the implementation of the inventive teaching. If the peptide is present in biotinylated form, and therefore demonstrates biotin as the tag, the anti-tag structure is streptavidin, i.e. a carrier coated with streptavidin. Other preferred tag/anti-tag pairs are: Protein A/immunoglobulin, GST (glutathione S transferase)/glutathione, Pin-Point (in vivo biotinylation)/avidin, thiorexidin/thiobond, PET (cellulose binding domain)/cellulose, and/or Pmal (maltose binding domain)/amylose, and others. Preferred carriers coated with anti-tag are selected from the group comprising carriers coated with streptavidin, glutathione, biotin, nickel-NTA, cellulose, amylose, thiobond, avidin, and/or immunoglobulin.

The inventive loops may be extracellular structures with which functional, agonistic, or antagonistic autoantibodies interact, detecting or binding them.

In a particular embodiment of the invention, the denaturing agent is ammonium sulfate. Of course, however, any denaturing agent that does not change the structure much can be used, such as alcohol in alcohol precipitation, for example. Advantageously, using ammonium sulfate or alcohol, it is possible to precipitate bodily fluids, such as serum, for example, particularly to precipitate them in fractionated manner. Thus, for example, antibodies, particularly autoantibodies, can be separated from other components of the bodily fluid. Denaturing of the bodily fluid takes place, in this connection, particularly in such a manner that the separated components can be returned to essentially the native state, or to a state that allows their detection, by means of methods known to a person skilled in the art. Of course, any denaturing agent known to a person skilled in the art, which is different from ammonium sulfate, or another denaturing agent that does not change the structure much is suitable for precipitating bodily fluids.

In another preferred embodiment of the invention, the carrier is a magnetic particle or an ELISA plate or another structure, which is suitable for incubating the mixture. Magnetic particles, in particular, permit the bound mixture to be separated using current or a magnetic charge. The use of ELISA plates preferably permits the use of laboratory routines and standardized equipment, since ELISA plates, particularly 96-well microtiter plates, are used as a standard in clinical and basic research.

In another preferred embodiment of the invention, the autoantibody is directed against a beta1-adrenergen receptor, a muscarinergen receptor, an angiotensin II AT1 receptor, an alpha1-adrenergen receptor, an endothelin IA receptor, a PAR-1, PAR-2, and/or PAR-3. Preferably, the receptors are G protein-coupled receptors.

In a particularly preferred embodiment of the invention, the autoantibodies directed against the beta1-adrenergen receptor are associated with dilatative myocardiopathy, Chagas' myocardiopathy, or myocarditis; the autoantibodies directed against the muscarinergen M2 receptor are associated with dilatative myocardiopathy or Chagas' cardiomyopathy; the autoantibodies directed against the angiotensin II AT1 receptor are associated with preeclampsia, or malignant hypertension; the autoantibodies directed against the alpha1-adrenergen receptor are associated with essential hypertension, refractory hypertension, pulmonary hypertension or psoriasis; and/or the autoantibodies directed against endothelin IA, PAR-1, PAR-2 and/or PAR-3 are associated with Raynaud's syndrome. Advantageously, these are autoimmune diseases in which the disease-associated autoantibodies are directed against certain extracellular structures of the G protein-coupled receptor. Such autoimmune diseases have been difficult or impossible to diagnose using previous means of laboratory routine, and, furthermore, can be treated with only significant effort, in some cases surgical effort (e.g. heart transplants or implantation of heart support systems), particularly, owing to the fact that individual tissue, organ regions, or complete organs are substituted by prostheses or other organs, for example, from living or dead patients.

In a very special embodiment of the invention, the peptide that comprises a sequence or partial sequence of the first and/or second loop of the receptor is used preferably in the detection of dilatative myocardiopathy, myocarditis, essential hypertension, refractory hypertension, pulmonary hypertension, or psoriasis; the peptide that comprises a sequence or partial sequence of the second loop of the receptor is preferably used for Chargas' myocardiopathy, dilatative cardiomyopathy, and Raynaud's syndrome. It is advantageously possible to use the first and/or second loop, or only the second loop, or peptides that comprise portions or fragments of the first and/or second loop, or only of the second loop, for detecting or treating the stated diseases. Advantageously, a person skilled in the art is given various possibilities for diagnosing, prognosticating, treating the stated autoimmune diseases, for follow-up treatment, or monitoring the progression of the treatment method, in each instance, during the course of treatment, by means of the disclosure of the connection between autoantibody, loop and the autoimmune disease, in each instance. The loops, i.e. the peptides that comprise partial regions of the loops, preferably are modified.

It is known to a person skilled in the art that individual amino acids demonstrate analogous physicochemical properties, which advantageously lead to the result that these amino acids can be substituted for one another. These include, for example, the group of amino acids (a) glycine, alanine, valine, leucine, and/or isoleucine; or the amino acids (b) serine and threonine; the amino acids (c) asparagines and glutamine; the amino acids (d) asparaginic acid and glutaminic acid; the amino acids (e) lysine and arginine; as well as the group of aromatic amino acids (f) phenyl alanine, tyrosine, and/or tryptophan. Amino acids within one and the same group (a-f) can be replaced for one another. Furthermore, it is possible that amino acids can be replaced by modified amino acids or specific enantiomers. Further modifications are possible of the teaching of WO99/62933 or WO02/38592.

In the state of the art, various possibilities for producing peptides are disclosed. Peptides that are designed proceeding from the inventive peptides, using such methods, are also covered by the inventive teaching. One possibility of generating function-analogous peptides is described, for example, in PNAS USA 1998, Oct. 13; 9521:12179-84, WO 99/62933, and/or WO 02/38592; these teachings are incorporated into the disclosure content of the invention. This means that all peptides, peptide fragments, or structures, which comprise peptides and were generated using the stated methods (proceeding from the inventive peptides) are peptides within the sense of the invention, if they accomplish the inventive task, particularly if they interact with the disease-causing autoantibodies. These autoantibodies can be, for example, agonistic autoantibodies, which activate receptors, or inhibitive antibodies.

In another preferred embodiment of the invention, it is preferred that the autoantibodies associated with dilatative cardiomyopathy are brought into contact with the peptide comprising a sequence or partial sequence of the first or second loop of the beta1-adrenergen receptor, the autoantibodies associated with Chargas' cardiomyopathy are brought into contact with the peptide comprising a sequence or partial sequence of the second loop of the beta1-adrenergen receptor, the autoantibodies associated with myocarditis are brought into contact with the peptide comprising a sequence or partial sequence of the first or second loop of the beta1-adrenergen receptor, the autoantibodies associated with dilatative cardiomyopathy are brought into contact with the peptide comprising a sequence or partial sequence of the second loop of the muscarinergen M2 receptor, the autoantibodies associated with Chargas' cardiomyopathy are brought into contact with the peptide comprising a sequence or partial sequence of the second loop of the muscarinergen M2 receptor, the autoantibodies associated with preeclampsia are brought into contact with the peptide comprising a sequence or partial sequence of the second loop of the angiotensin II AT1 receptor, the autoantibodies associated with malignant hypertension are brought into contact with the peptide comprising a sequence or partial sequence of the second loop of the angiotensin II AT1 receptor, the autoantibodies associated with essential hypertension are brought into contact with the peptide comprising a sequence or partial sequence of the first or second loop of the alpha1-adrenergen receptor, the autoantibodies associated with refractory hypertension are brought into contact with the peptide comprising a sequence or partial sequence of the first or second loop of the alpha1-adrenergen receptor, the autoantibodies associated with pulmonary hypertension are brought into contact with the peptide comprising a sequence or partial sequence of the first and/or second loop of the alpha1-adrenergen receptor, the autoantibodies associated with psoriasis are brought into contact with the peptide comprising a sequence or partial sequence of the first and/or second loop of the alpha 1-adrenergen receptor, and/or the autoantibodies associated with Raynaud's syndrome are brought into contact with the peptide comprising a sequence or partial sequence of the second loop of the endothelin IA, PAR-1 and/or PAR-2.

In another preferred embodiment of the invention, the IgG subclasses are the IgG1, IgG2, IgG3 and/or IgG4 subclasses. Advantageously, specific subclasses are used in order to detect disease-associated autoantibodies in simple and effective manner. In this way, simple and more reliable detection of autoantibodies can be performed, in contrast to the method without the use of specific subclasses. Surprisingly, the subclasses can be assigned to specific disease profiles. Accordingly, essentially no mixture of IgG subclasses is associated with a disease profile, which is surprising in that in the course of the generation of subclasses by Switch and others, biochemical mechanisms of different subclasses are generated.

In another advantageous embodiment, it is preferred that in the case of dilatative cardiomyopathy, the IgG3 and/or IgG4 subclasses are used, if the peptide comprises a sequence or partial sequence of the first loop, and the IgG1 subclass is used if the peptide comprises a sequence or partial sequence of the second loop, in the case of Chagas' cardiomyopathy, the IgG1, IgG2, IgG3 and/or IgG4 subclasses are used, in the case of myocarditis, the IgG3 and/or IgG4 subclasses are used if the peptide comprises a sequence or partial sequence of the first loop, and the IgG1 subclass is used if the peptide comprises a sequence or partial sequence of the second loop, in the case of preeclampsia, the IgG3 subclass is used, in the case of malignant hypertension, the IgG1 and/or IgG3 subclasses are used, in the case of essential hypertension, the IgG1 and/or IgG3 subclasses are used if the peptide comprises a sequence or partial sequence of the first loop, and the IgG2 subclass is used if the peptide comprises a sequence or partial sequence of the second loop, in the case of refractory hypertension, the IgG1 and/or IgG3 subclasses are used if the peptide comprises a sequence or partial sequence of the first loop, and the IgG2 subclass is used if the peptide comprises a sequence or partial sequence of the second loop, in the case of pulmonary hypertension, the IgG1, IgG2, and/or IgG3 subclasses are used, in the case of psoriasis, the IgG1, IgG2, IgG3 and/or IgG4 subclasses are used, and/or in the case of Raynaud's syndrome, the IgG1 subclass is used.

By means of this embodiment of the invention, an IgG subclass or subclasses can be made available for a specific autoimmune disease or for the autoantibodies, with which autoantibodies can be detected in simple and reliable manner.

In another preferred embodiment of the invention, the autoantibodies are concentrated or purified before being identified, using methods known to a person skilled in the art.

In a special embodiment of the invention, the method for concentrating or purifying the autoantibodies comprises the following steps:

a) Obtaining an IgG fraction from bodily fluid, b) Bringing the IgG fraction that was obtained into contact with a peptide that comprises a partial sequence of a first or second loop of a G protein-coupled receptor, whereby a mixture is obtained, c) Incubating the mixture with a carrier that is washed and concentrated, and d) Eluting the autoantibodies from the concentrated carrier.

Appropriately, a very reliable diagnosis or detection of the autoantibodies becomes possible by the purification or concentration.

In a special embodiment of the invention, the peptide that comprises the sequence or partial sequence of the first and/or second loop is selected from the group comprising:

EYGSFF [SEQ ID NO: 1], SFFCEL [SEQ ID NO: 2], ARRCYND [SEQ ID NO: 3], PKCCDF [SEQ ID NO: 4], AESDE [SEQ ID NO: 5], CYIQFF [SEQ ID NO: 6], EDGECY [SEQ ID NO: 7], VRTVEDGECYIQFFSNAAVTFGTAI [SEQ ID NO: 8], AFHYESQ [SEQ ID NO: 9], ENTNIT [SEQ ID NO: 10], FWAFGR [SEQ ID NO: 11], GRAFCDV [SEQ ID NO: 12], ITEEAGY [SEQ ID NO: 13], ERFCGI [SEQ ID NO: 14], GRIFCD [SEQ ID NO: 15] and/or ITTCHDVL [SEQ ID NO: 16].

In particular, these peptides can be assigned as follows (see also Table 3):

-continued

| | | |
|---|---|---|
| β1 DCM | I loop | EYGSFF [SEQ ID NO: 1], SFFCEL [SEQ ID NO: 2] |
| β1 DCM | II loop | ARRCYND [SEQ ID NO: 3], PKCCDF [SEQ ID NO: 4] |
| β1 myocard. | I loop | EYGSFF [SEQ ID NO: 1], SFFCEL [SEQ ID NO: 2] |
| β1 myocard. | II loop | ARRCYND [SEQ ID NO: 3], PKCCDF [SEQ ID NO: 4] |
| β1 Chagas | II loop | AESDE [SEQ ID NO: 5] |
| Musc. M2 DCM | II loop | CYIQFF [SEQ ID NO: 6], EDGECY [SEQ ID NO: 7] |
| Musc. M2 DCM | II loop | VRTVEDGECYIQFFSNAAVTFGTAI [SEQ ID NO: 8] |
| AT1 preecl. | II loop | AFHYESQ [SEQ ID NO: 9] |
| AT1 humor. kidney rej. | II loop | ENTNIT [SEQ ID NO: 10], AFHYESQ [SEQ ID NO: 9] |
| AT1 malign. hyp. | II loop | ENTNIT [SEQ ID NO: 10], AFHYESQ [SEQ ID NO: 9] |
| α1A essent. hyp. | I loop | FWAFGR [SEQ ID NO: 11], GRAFCDV [SEQ ID NO: 12] |
| α1A essent. hyp. | II loop | ITEEAGY [SEQ ID NO: 13] and ERFCGI [SEQ ID NO: 14] |
| α1A pulm. hyp. | I loop | FWAFGR [SEQ ID NO: 11], GRAFCDV [SEQ ID NO: 12] |
| α1A pulm. hyp. | II loop | ITEEAGY [SEQ ID NO: 13] and ERFCGI [SEQ ID NO: 14] |
| α1A refract. hyp. | I loop | FWAFGR [SEQ ID NO: 11], GRAFCDV [SEQ ID NO: 12] |
| α1A refract. hyp. | II loop | ITEEAGY [SEQ ID NO: 13] and ERFCGI [SEQ ID NO: 14] |
| α1B psoriasis | I loop | GRIFCD [SEQ ID NO: 15] |
| α1A psoriasis | I loop | GRAFCDV [SEQ ID NO: 12] |
| PAR-1 and PAR-2 | II loop | ITTCHDVL [SEQ ID NO: 16] |

Endothelin IA; Raynaud's Syndrome.

It is, of course, known to a person skilled in the art that, on the basis of the disclosure of specific sequence segments of the loop, sequences that flank the stated sequences in the naturally occurring loop can be used. Furthermore, it is known to a person skilled in the art that the sequences can be modified by deletions, substitutions, additions, insertions, or other biochemical or biophysical processes in such a manner, that individual parameters of these sequences (for example their action as a diagnostic or therapeutic agent) can be improved.

In another preferred embodiment of the invention, the peptide, in particular, is immobilized. In the sense of the invention, immobilization is understood to mean various methods and techniques for fixing the peptides in place on specific carriers. The immobilization can serve, for example, to stabilize the peptides, so that they are not reduced in their activity or disadvantageously modified by biological, chemical, or physical effects, particularly during storage or when mixed as a one-time batch. By means of the immobilization of the peptides, repeated use under technical or clinical routine conditions is possible; furthermore, a sample (preferably blood components) can continuously be mixed with at least one of the inventive peptides. This can be achieved, in particular, by means of various immobilization techniques, whereby binding of the peptides to other peptides or molecules, or to a carrier, takes place in such a manner that the three-dimensional structure, particularly at the center, which mediates the interactions with the autoantibodies, of the corresponding molecules, particularly the peptides, is not changed. Advantageously, the specificity to the autoantibodies of the patients is not lost by means of the immobilization. In the sense of the invention, three fundamental methods for immobilization can be used:

(i) Lateral crosslinking: In lateral crosslinking, the peptides are fixed in place with one another, without any detrimental effect on their activity. They are advantageously no longer soluble because of the lateral crosslinking.

(ii) Binding to a carrier: Binding to a carrier takes place, for example, by means of adsorption, ion binding, or covalent binding. This can also take place within microbial cells or liposomes, or other closed or open structures that contain membranes. The peptides are advantageously not influenced in their activity by being fixed. The peptides can advantageously be used in the clinic, for example, in diagnosis or treatment, multiple times or continuously, in carrier-bound manner.

(iii) Inclusion: Inclusion takes place, in the sense of the invention, in particularly, on a semi-permeable membrane, in the form of gels, fibrils, or fibers. Encapsulated peptides are separated from the surrounding sample solution, by means of a semi-permeable membrane, in such a manner that they advantageously can still react with the autoantibodies or with fragments thereof. Various methods are available for immobilization, such as adsorption on an inert or electrically charged inorganic or organic carrier. Such carriers can be, for example, porous gels, aluminum oxide, betonide, agarose, starch, nylon, or polyacrylamide. In this connection, immobilization takes place by means of physical bonding forces, often with the involvement of hydrophobic interactions and ionic bonds. Such methods are advantageously simple to handle and they influence the conformation of the peptides only to a slight extent. By means of electrostatic binding forces between the charged groups of the peptides and the carrier, the bond can advantageously be improved, for example by means of the use of ion exchangers, particularly Sephadex.

Another method is covalent bonding to carrier materials. For this purpose, the carrier groups can have reactive groups that enter into homeopolar bonds with amino acid side chains. Suitable groups in peptides are carboxy, hydroxy, and sulfide groups, and, in particular, the end-position amino groups of lysines. The surface of microscopic, porous glass particles can be activated by means of treatment with silanes, and subsequently reacted with peptides. Hydroxy groups of natural polymers can be activated with bromine cyan, for example, and subsequently coupled with peptides. Numerous peptides can advantageously enter into direct covalent bonds with polyacrylamide resins. In the inclusion in three-dimensional networks, the peptides are enclosed in ionotrophic gels or other structures known to a person skilled in the art. The pores of the matrix are, in particular, structured in such a manner that the peptides are retained and an interaction with the target molecules is possible. In the case of lateral crosslinking, the peptides are converted into polymer aggregates by means of crosslinking with bifunctional agents. Such structures are gelatinous and easily deformable, and are particularly suitable for use in different reactors. By adding other inactive ingredients, such as gelatin, for example, in crosslinking, the mechanical and bonding properties can advantageously be improved. In microencapsulation, the reaction space of the peptides is restricted, using membranes. Microencapsulation can take place, for example, as border surface polymerization. By means of immobilization during microencapsulation, the peptides become insoluble and therefore can be used again. In the sense of the invention, immobilized peptides are all peptides that are in a state that allows their re-use. The restriction of mobility and solubility of the peptides in chemical, biological, or physical manner advantageously results in low process costs, particularly in the elimination of autoantibodies from blood components.

In another preferred embodiment of the invention, the peptide is bound to a solid phase. Binding of the peptide to the solid phase can take place by way of a spacer. All chemical compounds that have the suitable structural and functional prerequisites for the function of the spacer can be used as spacers, as long as they do not modify the bonding behavior in such a manner that a bond between the autoantibody and the peptide is impaired in disadvantageous manner.

In a particularly preferred embodiment of the invention, the peptide comprises amino groups, amides, acetyl groups, biotin groups, markers, spacers, linkers, GKK and/or SGKK. Such structures advantageously allow use of the peptides in apheresis therapy.

In a particularly preferred embodiment of the invention, the linker and/or the spacer comprises α-amino carboxylic acids as well as their homo-oligomers and hetero-oligomers; α,ω-amino carboxylic acids as well as their branched homo-oligomers and hetero-oligomers; other amino acids as well as the linear and branched homo-oligomers and hetero-oligomers; amino-oligoalkoxy alkyl amines; maleinimido carboxylic acid derivatives; oligomers of alkyl amines; 4-alkylphenyl derivatives; 4-oligoalkoxy phenyl or 4-oligoalkoxy phenoxy derivatives; 4-oligoalkyl mercaptophenyl or 4-oligoalkyl mercaptophenoxy derivatives; 4-oligoalkyl aminophenyl or 4-oligoalkyl aminophenoxy derivatives; (oligoalkylbenzyl) phenyl or 4-oligoalkylbenzyl phenoxy derivatives as well as 4-oligoalkoxy benzyl phenyl or 4-oligoalkoxybenzyl phenoxy derivatives; trityl derivatives; benzyloxyaryl or benzyloxyalkyl derivatives; xanthen-3-yl oxyalkyl derivatives; (4-alkyl phenyl) or ω-(4-alkyl phenoxy) alkanic acid derivatives; oligoalkyl phenoxy alkyl or oligoalkoxy phenoxy alkyl derivatives; carbamate derivatives; amines; trialkyl silyl or dialkyl alkoxy silyl derivatives; alkyl or aryl derivatives and/or combinations thereof.

In another particularly preferred embodiment of the invention, the immobilized peptides are modified by means of deletion, addition, substitution, translocation, inversion and/or insertion.

The invention also relates to a peptide selected from the group comprising EYGSFF and/or SFFCEL (DCM, $1^{St}$ loop); ARRCYND and/or PKCCDF (DCM, $2^{nd}$ loop); AESDE (Chagas, $2^{nd}$ loop); CYIQFF and/or EDGECY (DCM, $2^{nd}$ loop); VRTVEDGECYIQFFSNAAVTFGTAI (Chagas, $2^{nd}$ loop); AFHYESQ (preeclampsia, $2^{nd}$ loop); ENTNIT and/or AFHYESQ (malignant hypertension, $2^{nd}$ loop); FWAFGR and/or GRAFCDV (essential hypertension, $1^{St}$ loop); ITEEAGY and/or ERFCGI (essential hypertension, $2^{nd}$ loop); GRIFCD, GRAFCDV (psoriasis, $1^{st}$ loop) and/or ITTCHDVL for use as a medicinal active ingredient. In the case of pulmonary and refractory hypertension, the statements concerning essential hypertension apply for the $1^{St}$ and $2^{nd}$ loop. Use as a therapeutic active ingredient in the sense of the invention means the use of the peptide or peptides in the entire field of medicine, preferably for the diagnosis and treatment of autoimmune diseases.

It is known to a person skilled in the art that he/she can generate additional function-analogous peptides on the basis of the disclosed peptides, as diagnosis and/or therapy agents. These function-analogous peptides are included in the inventive teaching. In particular, reference is made to the dissertation PNAS USA 1998, Oct. 13; 9521:12179-84, WO 00/6293 and/or WO 02/38592, which are incorporated into the disclosure content of the inventive teaching.

In a preferred embodiment of the invention, the peptide is bound by autoantibodies of patients having one of the following diseases: dilatative cardiomyopathy, Chagas' cardiomyopathy, myocarditis, preeclampsia, malignant hypertension, essential hypertension, refractory hypertension, pulmonary hypertension, psoriasis and/or Raynaud's syndrome. A person skilled in the art can make diagnosis and treatment methods available from this disclosure, by means of routine experiments.

The invention also relates to recognition molecules that are directed at the inventive peptide. Preferably, the recognition molecules are antibodies, antisense constructs and/or a chelators The recognition inventive molecules can be antibodies that are directed against autoantibodies that particularly induce the following diseases: dilatative cardiomyopathy, Chagas' cardiomyopathy, myocarditis, preeclampsia, malignant hypertension, essential hypertension, refractory hypertension, pulmonary hypertension, psoriasis and/or Raynaud's syndrome.

The invention also relates to a pharmaceutical composition that comprises the peptides and/or the recognition molecules, if applicable with a pharmaceutically compatible carrier. The pharmaceutical composition can be used, in particular, as a medication. For this purpose, it is possible, for example, to modify the peptides, by means of cyclization or other methods known to a person skilled in the art, in such a manner that they cannot be destroyed by peptide-decomposing structures inherent to the body, such as serum proteases, for example. By means of the use of the peptides or recognition inventive molecules, it is possible to neutralize the autoantibodies in vivo or ex vivo, or in vitro. In vitro neutralization is advantageous, for example, in the investigation of autoimmune diseases in tissue cultures or cell cultures. In the case in vivo neutralization, the medications are administered to the patient directly, while in the case of ex vivo neutralization, the blood is passed out of the body by way of a loop (for example in the form of a hose circulation), consequently brought into contact with the medication, and after neutralization has taken place, the autoantibody is passed back into the organism, particularly the human patient. In the sense of the invention, both those pharmaceutical compositions that are used for therapeutic and prophylactic purposes and those pharmaceutical compositions that can be used as diagnostic agents are considered to be medications.

Medications or pharmaceutical compositions, terms that are used synonymously here, are, pursuant to the invention, substances and formulations of substances that are intended to heal, alleviate, or prevent diseases, illnesses, bodily harm, or pathological symptoms, by being used on or in the human body. Medicinal ancillary substances are, pursuant to the invention, those substances that are used for the production as active ingredients of medications. Pharmaceutical technology ancillary substances serve for suitable formulation of the medication or the pharmaceutical composition, and can even be removed later, if they are only required during the production process, or can be part of the pharmaceutical composition as a pharmaceutically compatible carrier. The formulation of the medication or formulation of the pharmaceutical composition takes place, if necessary, in combination with the pharmaceutically compatible carrier and/or dilutant. Examples of suitable pharmaceutically compatible carriers are known to a person skilled in the art and comprise, for example, phosphate-buffered saline solutions, water, emulsions such as oil/water emulsions, for example, various types of detergents, sterile solutions, etc. Medications that comprise such carriers can be formulated by means of known, conventional methods. These medications or pharmaceutical compositions can be administered to an individual in a suitable dose, for example in a range from 1 µg to 10 g peptides per day and patient. In this connection, doses of 1 mg to 1 g are preferred. Administration of the fewest and lowest possible doses is preferred, and furthermore, a one-time dose is preferred. Administration can take place in different ways, for example in intravenous, intraperitoneal, intrarectal, intragastrointestinal, intranodal, intramuscular, local, but also subcutaneous, intradermal manner, or on the skin or by way of the mucous membranes. Administration of nucleic acids that code for the inventive peptide can also take place in the form of gene therapies, for example by way of viral vectors. The type of dosage and the administration path can be determined by the treating physician, in accordance with the clinical factors. It is known to a person skilled in the art that the type of dosage is dependent on various factors, such as, for example, height, body surface, age, gender, or the general health of the patient, but also on the special agent that is being administered, the duration and method of administration, and on other medications that might be administered in parallel. A person skilled in the art can orient himself/herself on the basis of the usual standard values as well as special teachings, for example the teaching of EP 1 085 955, which is incorporated into the disclosure content of the invention. Furthermore, it is known to a person skilled in the art that he/she can first diagnose the concentration of the autoantibodies with the inventive peptides, in order to determine the necessary concentration of the medication.

The pharmaceutical compositions or the medication particularly comprise a pharmacological substance that contains one or more inventive peptides or recognition molecules and/or nucleic acid molecules that code for them, in a suitable solution or administration form. These can be administered either alone, with the corresponding ancillary substances described under medications or pharmaceutical compositions, or in combination with one or more adjuvants, for example QS-21, GPI-0100 or other saponines, water/oil emulsions such as montanide, for example, adjuvants, polylysine, polyarginine compounds, DNA compounds such as CpG, for example, detox, bacterial vaccines such as typhus vaccine or BCG vaccine, for example, salts such as calcium phosphates, for example, and/or another suitable substance for enhancing effect; preferably immune-stimulating molecules such as interleukins, for example IL-2, IL-12, IL-4 and/or growth factors, for example GM-CSF. These are mixed with the inventive peptides or recognition molecules, using known methods, and administered in a suitable formulation and dosage. Formulations, dosages, and suitable components are known to a person skilled in the art.

The pharmaceutical composition or the medication can, of course, also be a combination of two or more of the inventive pharmaceutical compositions or medications, as well as a combination with other medications, such as, for example, antibody therapies, chemotherapies, or radiotherapies, which are administered or applied at the same time or separately, in suitable manner. The production of the medications or pharmaceutical compositions takes place using known methods.

The invention also relates to a kit that comprises the inventive peptide, the inventive recognition molecules, and/or the inventive pharmaceutical composition, if necessary with instructions for combining the contents of the kit and/or for making available a formulation for a recipient and an algorithm for administration of the formulation, in other words in what dose or at what time intervals individual components of the kit are to be administered to a patient. The recipient in the sense of the invention can, however, also be a cell or a tissue in vivo, ex vivo, or in vitro. The information can be, for example, a package insert, but also information that can be called up by the use by phone or via the Internet. The algorithm for administration of the formulation particularly includes instructions regarding the diagnostic and/or therapeutic method for treatment of a patient. This can be a single-stage or also multi-stage method, as well as methods that are carried out in the absence or the presence of the physician. This means that the therapy plan, i.e. the information about the latter, is preferably a component of the kit.

The invention also relates to a device for chromatography that comprises the inventive peptides.

In a preferred embodiment, the peptides are bound to a solid phase, for example, within the chromatography system.

The inventive device can be used, in particular, to eliminate the autoantibodies from fluids of a patient, i.e. to neutralize the autoantibodies. This method is known to a person skilled in the art under the term of immune adsorption or apheresis therapy. Using immune adsorption, immunoglobulins are removed from the patient's blood. Advantageously, this immune adsorption treatment can be performed on an inpatient or out-patient basis. It can be provided that the device, particularly the so-called adsorber, is a component of an extracorporal blood circulation. In this connection, blood is continuously or discontinuously taken from a larger blood vessel of the patient, particularly an arm vein, and separated into individual components, such as the cellular and humoral components, for example, by means of filtration or centrifugation. A significant component of the blood that is obtained thereby is, in particular, blood plasma. The blood plasma can advantageously be passed through the inventive device and, after adsorption of the autoantibodies, be given back to the patient, together with the blood components separated previously, particularly the cellular components, particularly through a different arm or leg vein. It can furthermore be provided that the peptides are immobilized on a sepharose matrix. This matrix can be placed into a container that has a volume from 10 to 400 ml. The blood plasma of the patient can then be passed over this matrix, whereby the autoantibodies are bound and can therefore be eliminated from the blood plasma. A person skilled in the art is aware of various possibilities for making available such peptides fixed on a solid phase, for example in the form of (i) adsorption columns capable of regeneration, in the form of (ii) double columns, as well as in the form of (iii) columns for one-time use. The various rinsing and elution solutions that allow a high level of efficiency of the treatment can easily be determined by a person skilled in the art, by means of routine experiments. By means of making available the inventive teaching, particularly the inventive peptides, various possibilities are disclosed to a person skilled in the art, for using these in vivo, ex vivo, and in vitro, for the prophylaxis, diagnosis, therapy, as well as follow-up treatment of dilatative cardiomyopathy, Chagas' cardiomyopathy, myocarditis, preeclampsia, malignant hypertension, essential hypertension, refractory hypertension, pulmonary hypertension, psoriasis and/or Raynaud's syndrome. Further embodiments are known to a person skilled in the art from WO 02/38592, EP 1 214 350, and WO 99/56126, which are incorporated into the disclosure content of the inventive teaching.

The invention also relates to the use of the inventive peptides, the inventive pharmaceutical composition, the inventive kit, and/or the inventive device, for the prophylaxis, diagnosis, therapy, monitoring of progression and/or follow-up treatment of autoimmune diseases selected from the group comprising dilatative cardiomyopathy, Chagas' cardiomyopathy, myocarditis, preeclampsia, malignant hypertension, essential hypertension, refractory hypertension, pulmonary hypertension, psoriasis and/or Raynaud's syndrome.

The invention also relates to the use of the inventive peptides, the inventive pharmaceutical composition, the inventive kit, and/or the inventive device, for the production of a medication for the treatment of autoimmune diseases selected from the group comprising dilatative cardiomyopathy, Chagas' cardiomyopathy, myocarditis, preeclampsia, malignant hypertension, essential hypertension, refractory hypertension, pulmonary hypertension, psoriasis and/or Raynaud's syndrome.

The invention also relates to the use of the inventive peptides, the inventive pharmaceutical composition, the inventive kit, and/or the inventive device, for screening medications. Screening of medications can comprise, for example, the identification of substances, particularly peptides, proteins, carbohydrates and/or lipids, which interact with the peptides. An interaction can be, for example, binding to these peptides, but also activation or inhibition of or by the stated peptides. Accordingly, a medication could be a structure, for example, that binds to the peptides in the body of a patient, and therefore to the corresponding loops, and thus competes for a binding site with the autoantibodies that occur there. By means of the disclosure of the inventive teaching, particularly by way of the disclosure of the connection between a disease and the binding location of the autoantibodies, a person skilled in the art can screen different medications. Screening of medications on the basis of disclosed targets belongs to the general knowledge of a person skilled in the art, and takes place by means of routine experiments; reference is made to the corresponding standard works in molecular biology and pharmacology.

The invention also relates to a method for treating an autoimmune disease selected from the group comprising dilatative cardiomyopathy, Chagas' cardiomyopathy, myocarditis, preeclampsia, malignant hypertension, essential hypertension, refractory hypertension, pulmonary hypertension, psoriasis and/or Raynaud's syndrome, by means of binding and/or removing autoantibodies by means of inventive peptides that are bound to a solid phase. By means of the peptides bound to the solid phase, the autoantibodies are bound, complexed and/or neutralized on the solid phase.

In a special embodiment of the treatment method, it is preferred that the autoantibodies are directed against beta1-adrenergic receptors in the case of dilatative cardiomyopathy, against beta1-adrenergic receptors in the case of Chagas' cardiomyopathy, against beta1-adrenergic receptors in the case of myocarditis, against muscarinergic M2 receptors in the case of dilatative cardiomyopathy, against muscarinergic M2 receptors in the case of Chagas' cardiomyopathy, against angiotensin II AT1 receptors in the case of preeclampsia, against angiotensin II AT1 receptors in the case of malignant hypertension, against alpha1-adrenergic receptors in the case of essential hypertension, against alpha1-adrenergic receptors in the case of refractory hypertension, against alpha1-adrenergic receptors in the case of pulmonary hypertension, against alpha1-adrenergic receptors in the case of psoriasis, and that the autoantibodies are directed against endothelin IA, PAR-1 and/or PAR-2 in the case of Raynaud's syndrome.

In the following, the invention will be explained in greater detail using an example, without being restricted to this example.

EXAMPLE

Identification of Angiotensin II AT1 Receptor Autoantibodies

Spontaneously beating, cultivated cardiomyocytes of newborn rats are a very useful model for studying the effect of autoantibodies.

Wallukat et al., 2001, already reported about studies of $\beta_1$ adrenoreceptor autoantibodies. This report concerns itself with angiotensin II $AT_1$ receptor autoantibodies in preeclamptic women. Preeclampsia is an illness that makes itself known by an increase in blood pressure and can result in death of the mother and the fetus. Dechend et al., 2000, were able to demonstrate the manifestation of agonistic antibodies against angiotensin $AT_1$ receptors that frequently occur in preeclamptic women. It was possible to explain many of the pathophysiological characteristics of preeclampsia with the activation of the $AT_1$ receptor by agonistic autoantibodies. The findings of Wallukat et al., 1999, show that immunoglobulin fractions and affinity-purified antibodies of preeclamptic women can stimulate the $AT_1$ receptor of cultivated cardiomyocytes. The beats per minute are reduced by adding Losartan (1 µM). It was possible to show, by means of neutralization experiments, that the IgG subclass 3 is responsible for the increase in heart rate.

Of these findings, an enzyme-coupled immune test for identifying angiotensin II $AT_1$ receptor autoantibodies (anti-$AT_1$-AAB) was developed.

First: Peptide solutions corresponding to the amino acid sequence of the second loop of the human $AT_1$ receptor (Sm 1986/1, 100 µg/ml), were incubated with anti-$AT_1$-AAB (1:1; vol./vol.) for 1 hour at 4° C. Anti-$AT_1$-AABs were produced by means of ammonium sulfate precipitation from waste fluids during birth (blood and isotonic saline solution). These samples had a stronger concentration than pure serum samples.

Second: This mixture was incubated with washed streptavidin-coated magnetic particles for 1 hour at 4° C.

Third: To separate the IgG/peptide mixture, the magnetic particles were washed three times with washing buffer (20 mM potassium phosphate buffer, 0.15 M CnCl, pH 7.5). The separation or washing can easily be performed using a magnet concentration apparatus (Dynal). Non-specific binding sites were blocked with 1% bovine serum albumin in washing buffer.

Fourth: The magnetic particles were incubated with a solution of horseradish peroxidase-marked antibodies against human IgG3 (1:200, 1 hour, room temperature).

Fifth: The particles were treated in the dark, at room temperature, for 30 min, using a standardized, ready-to-use solution of TMB (tetramethyl benzidine). The color reaction (blue-green) was stopped using 0.1 N HCl (yellow-orange). The optical density values were measured in a microplate reader (Anthos HTII) at 492 nm (reference filter 620 nm). The results are listed in Table 1.

The same peptide of the human $AT_1$ receptor (Sm 1986/1) was used to purify anti-$AT_1$-AABs. IgG solutions were mixed with peptide solution (100 µg/ml, 1:1; vol./vol.) and incubated at 4° C. for one hour. The streptavidin-coated magnetic particles that had been washed three times were added (300 µl). The particles were collected using a magnet concentration apparatus. The top fractions were carefully removed and stored in ice. The magnetic particles were washed three times and eluted with 3 M potassium thiocyanate solution for 15 min at room temperature. After magnetic concentration, the solutions were carefully separated and dialyzed in phosphate-buffered solution, against NaCl (0.9%), together with the first top fraction. After replacement five times within three days, the protein content was determined on the basis of the optical density (280 nm). The chronotropic effect of the top fraction and eluate on primary cultivated cardiomyocytes of newborn rats (bioassay) was recorded using an imaging computer system (IMAGOQANT).

Table 2 shows the reproducibility of the purification method. Six of the six purified anti-$AT_1$-ABBs showed the increase in heart rate/min (>24.4). Cultures treated with top fraction, on the other hand, result in no change or only moderate changes in the heart rate (<10.0).

The method of coimmunoprecipitation of the $AT_1$ receptor was similar to the method for the $B_1$ adrenoreceptor (Wallukat, 2001). The differences are: lysed membranes of transfected CHO cells (Couchon, 1997) were used for the coimmunoprecipitation. The lysed membranes should be freshly produced. The proteins were identified using an antibody against a peptide having the sequence of the N-terminal part of the $AT_1$ receptor, which had been produced in rabbits (N10, 1:100, Santa Cruz), and identified by means of Western blot and ECL system, with anti-rabbit IgG peroxidase:conjugates (1:10,000, Sigma).

FIG. 1 shows the results of the Western blot. It was possible to precisely detect a band (molecular weight>40.0 kDa), using internal positive samples (lysed membranes of transfected CHO cells and human placenta tissue). In earlier experiments (Neichel, non-published data), it was possible to block this band by means of the peptides that were used for producing the N10 antibodies. This band was missing in pure sepharose samples and in the top fractions of the purification experiments.

The results show the usefulness of the imaging computer system IMAGOQANT in detecting the increase in the beats/min caused by $AT_1$-ABBs in patients having preeclampsia. The enzyme-coupled immune test should also be checked with sera from preeclampsia patients and healthy donors. The purified $AT_1$-ABBs can be used for further investigation of the pathogenesis of preeclampsia.

TABLE 1

Measurement of the AT1 autoantibodies using an enzyme-coupled immune test

| IgG | n | Optical density (OD, 492 nm) Range |
|---|---|---|
| Healthy test subjects (controls) | 3 | 0.036-0.069 |
| Preeclamptic woman | | |
| Positive | 15 | 0.071-0.786 |
| Negative | 4 | 0.021-0.069 |

TABLE 2

Influence of top fractions and eluates of the magnetic particles on the heart rate of cultivated cardiomyocytes of newborn rats

| Patient/ Date of experiment | Samples | OD | µg/ml | Bioassay (increase in beats/min) | | |
|---|---|---|---|---|---|---|
| D. Mar. 19, 2002 | top fraction | 4.300 | 3071.4 | 6.0 ± 0.0 | 6.0 ± 0.0 | 10.0 ± 1.6 |
| | eluate | 0.086 | 61.4 | 12.8 ± 1.6 | 27.6 ± 2.0 | 34.4 ± 1.2 |
| D. May 27, 2002 | top fraction | 6.820 | 4871.4 | −1.6 ± 0.8 | 4.0 ± 1.2 | 6.4 ± 1.2 |
| | eluate | 0.033 | 23.6 | 12.1 ± 2.4 | 18.9 ± 0.8 | 24.5 ± 0.8 |
| D. Jun. 3, 2002 | top fraction | | | 3.3 ± 0.8 | 3.2 ± 0.8 | 4.7 ± 1.6 |
| | eluate | 0.0104 | 74.3 | 11.1 ± 1.2 | 15.2 ± 2.0 | 33.9 ± 2.0 |

±SD from average value

TABLE 3

Autoantibodies against G protein-coupled receptors
Information concerning the epitopes and IgG subclass

| Antibodies against rec. | Disease | Epitope | IgG subclass |
|---|---|---|---|
| Beta1-adren. | Dilat. cardiomyopathy | 1st loop | IgG3 and IgG4 |
| | | 2nd loop | IgG1 |
| Beta1-adren. | Chagas' cardiomyopathy | 1st loop | IgG3 and IgG4 |
| | | 2nd loop | IgG1 |
| Beta1-adren. | Myocarditis | 1st loop | IgG3 and IgG4 |
| | | 2nd loop | IgG1 |
| Muscarin. M2 | Dilat. cardiomyopathy | 2nd loop | IgG1 |
| Muscarin. M2 | Chagas' cardiomyopathy | 2nd loop | |
| Ang. II AT1 | Preeclampsia | 2nd loop | IgG3 |
| Ang. II AT1 | Malignant hypertension | 2nd loop | IgG1 and IgG3 |
| Alpha1-adren. | Essential hypertension | 1st loop | IgG1 and IgG3 |
| | | 2nd loop | IgG2 |
| Alpha1-adren. | Refractory hypertension | 1st loop | IgG1 and IgG3 |
| | | 2nd loop | IgG2 |
| Alpha1-adren. | Pulmonary hypertension | 1st loop | IgG1 and IgG3 |
| Alpha1-adren. | Psoriasis | 1st loop | IgG2 |
| | | 2nd loop | |
| PAR-1 and PAR-2 Endothelin IA | Raynaud's syndrome | 2nd loop | IgG1 |

Key

FIG. 1: Western blot of the coimmunoprecipitation of the angiotensin $AT_1$ receptor Track 1 protein A/sepharose; 2 preeclamptic patient D. without purification; 3 KSCN eluate; 4 top fraction; 5 lysed CHO membrane; 6 lysed placenta tissue.

---

The invention claimed is:

1. Method for detecting disease-associated autoantibodies, which are directed at G protein-coupled receptors for diagnosis of autoimmune diseases, comprising
   a) bringing bodily fluid into contact with an agent for precipitating autoantibodies, wherein a fraction of said fluid comprising said autoantibodies is precipitated and wherein said autoantibodies are, upon precipitation, returned to essentially their native state,
   b) bringing the precipitated fraction into contact with a peptide comprising
   a sequence or partial sequence of the first and/or second loop of a G protein-coupled receptor and a tag, whereby a mixture is formed in which the autoantibodies bind said sequence or partial sequence of said peptide,
   c) incubating the mixture with a carrier coated with an anti-tag to bind said tag,
   d) washing the carrier,
   e) incubating the carrier with anti-IgG antibody subclasses, wherein the anti-IgG antibody is marked for an enzyme reaction or color reaction, and
   f) carrying out said enzyme reaction or color reaction
   to detect disease-associated autoantibodies, which are directed at said G protein-coupled receptor to diagnose said diseases,
   wherein the peptide that comprises a sequence or partial sequence of the first and/or second loop of the receptor is used in the detection of autoantibodies associated with dilatative cardiomyopathy, myocarditis, essential hypertension, refractory hypertension, pulmonary hypertension, or psoriasis, and that the peptide that comprises a sequence or partial sequence of the second loop of the receptor is used for Chargas' myocardiopathy, dilatative myocardiopathy, and/or Raynaud's syndrome.

2. Method of claim 1,
   wherein the agent for precipitating autoantibodies is ammonium sulfate and/or alcohol.

3. Method of claim 1,
   wherein the carrier is a magnetic particle or an ELISA plate.

4. Method of claim 1,
   wherein the autoantibodies are directed against a beta1-adrenergen receptor, a muscarinergen M2 receptor, an alpha1-adrenergen receptor, and an endothelin IA receptor, a PAR-1, PAR-2, and/or PAR-3.

5. Method of claim 4,
   wherein the autoantibodies directed against the beta1-adrenergen receptor are associated with dilatative myocardiopathy, Chagas' myocardiopathy, or myocarditis; the autoantibodies directed against the muscarinergen M2 receptor are associated with dilatative myocardiopathy and/or Chagas' cardiomyopathy; the autoantibodies directed against the alpha1-adrenergen receptor are associated with essential hypertension, refractory hypertension, pulmonary hypertension and/or psoriasis; and/or the autoantibodies directed against endothelin IA receptor, PAR-1, PAR-2 and/or PAR-3 are associated with Raynaud's syndrome.

6. Method of claim 1,
   wherein
   the autoantibodies associated with dilatative cardiomyopathy are brought into contact with the peptide comprising a sequence or partial sequence of the first and/or second loop of the beta1-adrenergen receptor,
   the autoantibodies associated with Chargas' cardiomyopathy are brought into contact with the peptide comprising a sequence or partial sequence of the second loop of the beta1-adrenergen receptor,
   the autoantibodies associated with myocarditis are brought into contact with the peptide comprising a sequence or partial sequence of the first and/or second loop of the beta1-adrenergen receptor,
   the autoantibodies associated with dilatative cardiomyopathy are brought into contact with the peptide comprising a sequence or partial sequence of the second loop of the muscarinergen M2 receptor,
   the autoantibodies associated with Chargas' cardiomyopathy are brought into contact with the peptide comprising a sequence or partial sequence of the second loop of the muscarinergen M2 receptor,
   the autoantibodies associated with essential hypertension are brought into contact with the peptide comprising a sequence or partial sequence of the first and/or second loop of the alpha1-adrenergen receptor,
   the autoantibodies associated with refractory hypertension are brought into contact with the peptide comprising a sequence or partial sequence of the first and/or second loop of the alpha1-adrenergen receptor,
   the autoantibodies associated with pulmonary hypertension are brought into contact with the peptide comprising a sequence or partial sequence of the first and/or second loop of the alpha1-adrenergen receptor,
   the autoantibodies associated with psoriasis are brought into contact with the peptide comprising a sequence or partial sequence of the first and/or second loop of the alpha1-adrenergen receptor,
   the autoantibodies associated with Raynaud's Syndrome are brought into contact with the peptide comprising a sequence or partial sequence of the first and/or second loop of the endothelin IA receptor, PAR-1, PAR-2 and/or PAR-3.

7. Method of claim 1,
   wherein the tag is biotin and the anti-tag is avidin or streptavidin.

8. Method of claim 1,
   wherein
   in case of dilatative cardiomyopathy, IgG3 and/or IgG4 subclasses are detected if the peptide comprises a sequence or partial sequence of the first loop, and/or the IgG1 subclass is detected if the peptide comprises a sequence or partial sequence of the second loop,
   in case of Chagas' cardiomyopathy, IgG1, IgG2, IgG3 and/or IgG4 subclasses are detected,
   in case of myocarditis, IgG3 and/or IgG4 subclasses are detected if the peptide comprises a sequence or partial sequence of the first loop, and/or the IgG1 subclass is detected if the peptide comprises a sequence or partial sequence of the second loop, in case of essential hypertension, IgG1 and/or IgG3 subclasses are detected if the peptide comprises a sequence or partial sequence of the first loop, and/or the IgG2 subclass is detected if the peptide comprises a sequence or partial sequence of the second loop, in case of refractory hypertension, IgG1 and/or IgG3 subclasses are detected if the peptide comprises a sequence or partial sequence of the first loop, and/or the IgG2 subclass is detected if the peptide comprises a sequence or partial sequence of the second loop, in case of pulmonary hypertension, IgG1, IgG2, IgG3 and/or IgG4 subclasses are detected, in the case of psoriasis, IgG1, IgG2, IgG3 and/or IgG4 subclasses are detected, and/or in case of Raynaud's Syndrome, IgG1 subclass is detected.

9. Method of claim 1,
wherein the autoantibodies are further concentrated or purified before being contacted with the peptide in b).

10. Method of claim 9,
wherein
the method for further concentrating or purifying the autoantibodies comprises:

i) bringing the IgG fraction that was obtained into contact with a peptide that comprises a partial sequence of a first or second loop of a G protein-coupled receptor and a tag, whereby a mixture is obtained in which the autoantibody binds said partial sequence of said peptide, ii) incubating the mixture with a carrier coated with an anti-tag to bind said tag and that is washed and concentrated, and iii) eluting the autoantibodies from the concentrated carrier.

11. Method of claim 1,
wherein the partial sequence of the first and/or second loop is selected from the group consisting of EYGSFF [SEQ ID NO: 1], SFFCEL [SEQ ID NO: 2], ARRCYND [SEQ ID NO: 3], and/or PKCCDF [SEQ ID NO: 4].

12. The method of claim 11, wherein the autoantibodies are associated with the dilative cardiomycopathy and are directed against a beta 1-adrenergen receptor and/or a muscarinergen M2 receptor.

13. The method of claim 1, wherein the peptide comprises a partial sequence of the first and/or second loop of the G protein-coupled receptor and a tag.

* * * * *